United States Patent [19]

Rogerson

[11] Patent Number: 4,562,024
[45] Date of Patent: Dec. 31, 1985

[54] PROCESS FOR PREPARING GRANULATE CONTAINING POORLY COMPRESSIBLE MEDICINALLY ACTIVE MATTER

[75] Inventor: Alan G. Rogerson, Newcastle, United Kingdom

[73] Assignee: Sterling Drug Inc., New York, N.Y.

[21] Appl. No.: 520,975

[22] Filed: Aug. 8, 1983

Related U.S. Application Data

[63] Continuation-in-part of Ser. No. 511,428, Jul. 6, 1983.

[30] Foreign Application Priority Data

Jul. 6, 1982 [GB] United Kingdom ............... 8219487
Jul. 5, 1983 [IE] Ireland ............................ 1577/83

[51] Int. Cl.$^4$ .............................................. C09C 1/56
[52] U.S. Cl. ................................ 264/117; 264/122; 264/128; 514/629; 514/562
[58] Field of Search ................ 264/117, 122, 129; 424/319

[56] References Cited

U.S. PATENT DOCUMENTS

| | | | |
|---|---|---|---|
| 2,877,159 | 3/1959 | Lachman et al. | 167/82 |
| 3,084,104 | 4/1963 | Tuerck et al. | 167/82 |
| 3,406,426 | 10/1968 | Pobst, Jr. et al. | 18/1 |
| 3,671,633 | 6/1972 | Sleth et al. | 264/122 |
| 3,705,019 | 12/1972 | Mesiah et al. | 23/313 |
| 3,789,119 | 1/1974 | Fusari et al. | 424/78 |
| 3,860,526 | 1/1975 | Corbett | 252/181 |
| 3,987,138 | 10/1976 | Hege | 264/117 |
| 4,132,753 | 1/1979 | Blichare et al. | 264/117 |
| 4,322,449 | 3/1982 | Voss et al. | 264/128 |

FOREIGN PATENT DOCUMENTS 1287431 8/1972 United Kingdom.
1390032 11/1972 United Kingdom.
1410809 10/1975 United Kingdom.

*Primary Examiner*—Jeffery Thurlow
*Assistant Examiner*—Patrick M. Dailey
*Attorney, Agent, or Firm*—Robert K. Bair; B. Woodrow Wyatt; Paul E. Dupont

[57] ABSTRACT

An improved wet granulation process for preparing compressed tablets, particularly those containing a poorly compressible medicament, e.g., paracetamol and derivatives thereof, the improvement which comprises homogenizing part only of particulate solid material including active matter and tabletting aids with at least 90% by weight of a predetermined quantity of granulating fluid, so as to form a substantially homogenous slurry wherein the percentage of weight of solids, both dissolved and undissolved, in the slurry is at least about 25% w/w; and then moistening the remaining part of the particulate solid material in the manner of wet granulation but with the slurry resultant from above (and thereafter with the balance of the granulating fluid, if any) so as thus to form a desired substantially uniform, moist, coherent, non-pasty mass ready for granulation. Said mass is then granulated and dried, and the dried granules compressed and compacted into tablets.

27 Claims, No Drawings

PROCESS FOR PREPARING GRANULATE CONTAINING POORLY COMPRESSIBLE MEDICINALLY ACTIVE MATTER

CROSS REFERENCE TO RELATED APPLICATION

This application is a continuation-in-part of copending application Ser. No. 511,428, filed July 6, 1983.

BACKGROUND OF THE INVENTION (a) Field of the Invention

This invention relates to an improved process for preparing tablets by a modified wet granulation technique; and especially, but not exclusively, tablets which have a high active matter content, in particular, tablets containing poorly compressible medicinally active matter.

(b) Information Disclosure Statement

A variety of substances meant to be taken by humans and other animals (especially, but not exclusively, pharmaceutical substances intended for oral administration) are often formulated as tablets.

The term "tablet" should be sufficiently familiar to require no explanation; but, in case of need, can be defined as follows. As used herein the term "tablet" includes not only tablets proper but also similar discrete bodies, perhaps of other shapes and sometimes known by different names, above all so called "caplets" (i.e. capsule-shaped tablets, which are easier than tablets to swallow) and also such things as lozenges, pills and dragees. The term is also used to refer to mixtures of particulate solid materials, which have been brought together in various ways and finally compressed so that they become compacted into shaped entities able to persist under normal handling conditions but to disintegrate at the desired site, usually within the body and above all in the digestive tract.

Most tablets are intended to be swallowed, and thus must be kept within the maximum bulk limit which (dependent slightly upon its shape) an average person is able and willing to swallow.

The "size" of the tablets they produce is conventionally defined by tabletters in terms not of their bulk but of their weight. There is room for debate as to what precisely is the absolutely maximum "swallowable" size of tablet, which must depend on the shape of the tablet and on the individual who is to swallow it. It is considered that the absolutely maximum "swallowable" size of tablet can be set at a weight of no more than say 1200 milligrams; and many might choose to set it much lower at a weight of not more that say about 850 mg. Whatever weight limit one adopts (be it 850 mg or 1200 mg, or something in between) it follows that any tablet which is to be swallowed must accommodate all its ingredients, not only the active matter but also every other necessary or desirable type of ingredient, within that weight limit. Moreover that consideration not only applies to tablets intended to be swallowed but to some extent also affects tablets of other kinds, because so much of the available tabletting machinery is dimensioned to produce swallowable tablets that it is often in practice most convenient to make other kinds of tablets on the same machinery and thus to the same dimensions.

For most purposes all necessary ingredients can be accommodated within an 850 mg tablet, and certainly within a 1200 mg tablet. There are however situations in which the above discussed overall weight limitation one tablet size creates a hitherto insurmountable obstacle.

In a pharmaceutical context, one can readily appreciate that the dose necessary at any one administration should desirably be given in the fewest possible tablets, thus if possible in just a single tablet. In the relatively rare event that the dose of active matter necessary at any one administration should exceed the maximum swallowable size of tablet, clearly it is then quite impossible for that dose to be contained in just one swallowable tablet. A much more common situation is however that the amount of active matter to be given at any one administration is less than the swallowable maximum, so that notionally it could all be contained within a single tablet and yet, in practice, that till now has proved impossible, because the amount of active matter so closely approaches the swallowable maximum that the balance is not enough to accommodate the tabletting aids (and possibly other ingredients) which are pharmacologically inert but whose presence is vital to the manufacture of a satisfactory tablet when, as so often, the compression characteristics of the active matter are poor.

In the manufacture of tablets, the final compression of each tablet takes place between the punches within a die, after the latter has been filled with the mixture of particulate solid materials, which however before it enters the die has normally been pregranulated. Such differences as exist between conventional tabletting techniques lie primarily in the respective procedures used for preliminary processing of the mixture of particulate solid materials before they enter the die. When all the ingredients, including the active matter, have good compression characteristics, one may be lucky enough to be able to adopt the simplest and cheapest of techniques known as dry granulation, or a modified version thereof involving what is called preliminary slugging. All too often however the compression characteristics of the mixture are so poor, a defect attributable usually to the nature and/or amount of active matter present, that one is driven back as a last resort on the technique known as wet granulation.

There is much art and skill in practicing the wet granulation technique; but, in outline, it involves no more than the incorporation of a granulating fluid into the mixed, powdery tablet ingredients (including at least some tabletting aids) in such an amount and manner as to convert them into a uniform, moist, coherent, non-pasty mass, which then is formed into moist granules of fairly uniform size, usually by forcing the mass through a screen. Thereafter the moist granules are dried and rescreened to break down agglomerates, and finally blended with other tabletting aids so as thus to arrive at the granulate ready for tabletting.

It will be noted that in wet granulation the tablet ingredients besides the active matter also conventionally include other, pharmacologically inert materials, certainly tabletting aids and perhaps also bulking agents. Some of such tabletting aids may be included in the mixed, powdery ingredients before the granulating fluid is incorporated therein, while further tabletting aids may be applied to the surfaces of the granules, and in between them, after the granules have been formed and before the granulate is passed to the tabletting machine.

At this point it should be observed that when the amount of active matter per tablet is small the pharmacologically inert materials conventionally might well include what are here described as bulking agents, that is to say filler type materials which serve no function except to bulk out the mixture so as to make tablets of adequate size; but that is not the kind of situation with which this invention is primarily concerned, and thus mere bulking agents are not intended to be included in the term "tabletting aids" as used herein.

In the kind of situation in which one resorts to a wet granulation technique, thus when the nature and/or amount of the active matter causes the mixture to have poor compression characteristics, it will however usually be necessary to incorporate some appropriate amount of some or all of the conventional types of tabletting aids, namely binders, glidants, lubricants and disintegrants. Broadly speaking:

the binders are substances which help bind the particles of powder together in a form suited to compaction and compression:

the glidants are substances which aid filling of the particles and/or granules into the die before compression;

the lubricants are substances which help the compressed tablets to leave the die; and the disintegrants are substances which help the tablet to disintegrate, and perhaps dissolve, when it reaches its ultimate destination, usually within the body.

Quite a variety of materials is available to serve each of these functions, some of them more effective than others. Sometimes a given material may be capable of simultaneously performing more than one function; and, of course, all of them cannot help but bulk out the tabletting mixture, even though that perhaps may not be desired. It will therefore be appreciated that one cannot make any wholly reliable predictions about the absolute and relative amounts of each individual binder and/or glidant and/or lubricant and/or disintegrant which should be present. In a successful formulation made by wet granulation one can however as a generalization say that the overall requirement for all four types of tabletting aids will nearly always fall in the range of from 5% to 25% w/w, calculated relative to the weight of the final (dry) powder mass; and indeed the overall percentage of tabletting aids usually need not exceed say 15% w/w.

Even using the conventional wet granulation technique it is however not always possible to achieve a successful formulation, that is, one which on compression of the granulate yields tablets which conform to accepted standards of hardness, fragility, disintegration and uniformity of weight, unless indeed the above indicated overall percentage of tabletting aids is still further increased. The problem does not usually lie with the tabletting aids themselves, for these can be chosen at will from the well tried array of such materials introduced over very many years, and can be relied upon to serve their function admirably, to the extent that they are not prevented from so doing by the nature of the active matter. It is indeed the active matter which is liable to cause tabletting problems, for here there is no freedom of choice—the tabletter must seek to incorporate in his tablet whatever active matter the clinician wants, and if possible in an amount which represents a unit dose suitable at one administration. While some kinds of active matter, at least when present in moderate proportions, will lend themselves readily to compression and compaction into good quality tablets when accompanied only to conventional proportions of tabletting aids others will not and as new kinds of active matter are introduced which have poor compression characteristics and/or as the clinician seeks to prescribe higher dose levels of existing kinds of poorly compressible active matter, the tabletter is faced with fresh problems, sometimes very difficult or indeed impossible to solve within the confines of a single tablet. Where high dosage active matter (or mixtures thereof) with poor compression characteristics must be incorporated into a single tablet, even conventional wet granulation techniques using normal levels of tabletting aids prove inadequate to resolve these problems; yet if one uses still higher levels of tabletting aids, that may well result in a mixture of such bulk volume that the required weight is difficult or impossible to accommodate within the compression die cavity. However, even if the mixture can be so accommodated and tablets compressed, the tablets then may be of such large size that they are difficult to swallow.

An example of a poorly compressible medicinally active substance is paracetamol (also known as acetaminophen). Illustrative of prior procedures for preparing tablets containing paracetamol are those described in British Pat. Nos. 1,287,431, 1,390,032 and 1,410,909.

The Aspro-Nicholas Ltd. British Pat. No. 1,287,431, published Aug. 31, 1972, discloses a process for preparing coated paracetamol particles suitable for direct compression into tablets comprising agitating particles of paracetamol and a binding agent in an aqueous medium to form a slurry and thereafter drying the resultant slurry to obtain discrete particles of paracetamol coated with said binding agent, the amount of binding agent being such that the dried particles are coated with from 2 to 5%, preferably 3 to 4% by weight of said binding agent and the ratio by weight of uncoated particles of paracetamol to the water in said medium being not greater than 5:1.

The Sterling-Winthrop Group Ltd. British Pat. No. 1,390,032, published Apr. 9, 1975, shows the method of preparing a free-flowing granular material suitable for tabletting which method comprises providing an aqueous fluid comprising: (a) more than 80% by weight of an N-acylaminophenol or ester thereof, and (b) dissolved in the aqueous fluid, from 1.5% to 10%, by weight on the weight of component (a), of a water-soluble polymeric organic binder, and spray-drying the aqueous fluid.

The Sterling-Winthrop Group Ltd. British Pat. No. 1,410,909, published Oct. 22, 1975, shows a method of preparing a composition containing paracetamol which is suitable for direct tablet compression, which method comprises rapidly providing an aqueous solution containing paracetamol, and from 1% to 15% by weight on the weight of the paracetamol, of a polymer selected from homopolymers and copolymers of vinyl acetate and vinyl pyrrolidone dissolved in said aqueous solution at a temperature of at least 95° C., and then immediately cooling this solution with gentle stirring and recovering the solid therefrom.

Thus, combination of poorly compressible medicinally active ingredients, such as paracetamol, with tabletting aids, which include polymeric binders, to produce a blend suitable for compression into tablets is known. It is the manner in which this combination is achieved by the process of this invention which is not obvious.

It is the problem of tabletting such poorly compressible kinds of active matter, and especially those which are clinically prescribed at high dosage levels, to which the instant invention pertains. Investigation of that problem led to questioning hitherto prevailing assumptions concerning the procedures employed in the formation of tablets, with the aim of finding some way of making good quality tablets even from poorly compressible kinds of active matter which tablets however contain no more than the unavoidable proportion of tabletting aids which need to be present in "successful" conventional formulations based on easily compressible active matter.

It now has been found surprisingly that by employing a modified version of conventional wet granulation, which for convenience is termed slurry granulation, there is provided a process for manufacturing tablets which achieves this much desired goal.

SUMMARY OF THE INVENTION

The invention relates to an improvement in a modified wet granulation process for making tablets, preferably those containing poorly compressible, medicinally active matter by compressing and compacting a suitable granulate, said improvement which comprises first homogenizing a prescribed part of the particulate solid material of the granulate with at least 90% by weight of a chosen amount of granulating fluid to form a substantially homogeneous slurry and then moistening the remaining part of the particulate solid material with said slurry to form a substantially uniform, moist, coherent, non-pasty mass ready for granulation. The invention also relates to the use of said improvement to produce successively improved granules and improved tablets.

DETAILED DESCRIPTION INCLUSIVE OF PREFERRED EMBODIMENTS

According to this invention there is provided, in a process for manufacturing tablets by compressing and compacting a suitable granulate, the method of preparing the granulate by forming an intimate mixture of particulate solid materials including active matter and tabletting aids, as well as optionally other pharmacologically inert materials, thereafter wet granulating said mixture by moistening it with substantially non-solvent (as hereinafter defined) granulating fluid to form a substantially uniform, moist, coherent, non-pasty mass which finally is granulated (i.e. subdivided into individual granules) and dried, these dried granules (optionally after adding further tabletting aids thereto) constituting the desired granulated ready for compression and compaction into tablets, the improvement which comprises:

(A) predetermining a quantity of granulating fluid needed to convert the entire particulate solid mixture into a desired moist, coherent, non-pasty mass;

(B) homogenizing part only of the particulate solid material, separately from the remainder thereof, with a chosen amount of granulating fluid, that chosen amount being at least 90% by weight of the aforesaid predetermined quantity of granulating fluid, so as to form a substantially homogeneous slurry wherein the percentage by weight of solids in the slurry, namely:

$$\frac{\text{(total solids, both dissolved and undissolved)} \times 100}{\text{total slurry, i.e., fluids plus total solids}}$$

is at least about 25%, preferably at least about 30% w/w; and (C) moistening the remaining part of the particulate solid material in the manner of wet granulation but with the slurry resultant from step (B) above (and thereafter with the balance of the granulating fluid, if any) so as thus to form a desired, substantially uniform, moist, coherent, non-pasty mass ready for granulation.

It will be seen that the process of this invention thus involves separately homogenizing part of the particulate solid material with the granulating fluid to form a substantially homogeneous slurry which is then used to moisten the remainder otherwise in the manner of conventional wet granulation. While it is at present not fully understood why this technique should enable lesser proportions of tabletting aids to be satisfactorily employed than would be needed in a conventional wet granulation, it is believed that homogenization of part of the ingredients somehow contributes to an improvement of the compression characteristics of the material in the slurry. It is reasonable to suppose that the overall compression characteristics of any granulate must partly depend upon the compression characteristics of each of its ingredients, which however may operate via more than one mechanism. Poorly compressible materials quite often have relatively fine particle sizes, and thus form low bulk-density "flocculent" powders, wherein a proportion of the particles are aggregated into multi-particle clumps. One may therefore speculate that homogenization perhaps tends to reduce the proportion of multi-particle clumps, and/or to ensure that substantially all of the particles are properly wetted with the granulating fluid. These however, are only suppositions, and the process of the invention is not to be limited by any theoretical considerations. In practice, the new slurry granulation process of the invention works in situations where the conventional wet granulation process does not.

It is convenient here to observe the term "active matter" is used throughout this specification in a broad sense which encompasses whatever the manufacturer may wish to characterize his tablets, thus for instance including either sweetening and flavoring agents in the case of confectionary products or dietary aids of the non-assimilable kind. The invention however is primarily concerned with medicinally active matter which consists of one or more medicinally active substances, as illustrated hereinbelow.

The predetermined "total" amount of granulating fluid to be employed (either in the granulating slurry as such, or otherwise) obviously must not exceed that needed to achieve the desired moist, coherent but non-pasty mass, since when that amount (which is partly dependent, as known to skilled tabletters, upon the degree of mechanical working imposed upon the mix during its preparation and subsequent screening) is exceeded then the mixture will clog during screening to form the moist granules. Equally however the predetermined "total" amount of granulating fluid to be employed cannot be less than the amount needed to achieve the desired moist, coherent, non-pasty mass.

Predetermination of the total quantity of granulating fluid needed to convert the entire particulate solid mixture into a desired substantially uniform, moist, coherent, non-pasty mass can and indeed initially will be achieved empirically, as is always the case in conventional procedures. Any skilled operative can usually make an intelligent guess at the approximate quantity of granulating fluid which will be required; but the exact amount is found by trial, adding a little at a time until the desired effect is achieved. Of course, the proper quantity of granulating fluid having once been determined for a certain mixture of ingredients it will not always be necessary to redetermine it subsequently. Repetition of the process in the same manner on the same batch-size of the same ingredients will require essentially the same, already predetermined quantities of granulating fluid. In such situations step (1) of the process of this invention becomes notional rather than actual but, even if only notionally, it does form part of the process.

In passing it should be noted that the quantity of granulating fluid required will of course be dependent, as in conventional wet granulation, upon the nature of the ingredients in the powdery mixture to be granulated, upon the parameters of the mixing procedure employed, and upon what sort of moist, coherent, non-pasty mass is required. As general guidance it can be said that the total amount of granulating fluid predetermined for use according to the present invention, although not necessarily exactly identical, will nevertheless be much the same as the amount needed to moisten the same mass using the conventional wet granlation technique. The exact amount of a granulating fluid to be employed is however a matter which can and indeed must ultimately be left, as in conventional wet granulation techniques, to the skill and judgement of the operative seeking to achieve the desired characteristics in the granulate and tablets compressed therefrom.

The homogenization of the particulate solid materials with the granulating fluid must, as indicated above, be carried out in such a way as to form a substantially homogeneous slurry, that is to say a suspension (having the specified, relatively high percentage w/w of solids) which shows no obvious externally visible sign of segregation over the longest period encountered as an acceptable delay in manufacturing procedures, thus in the course of a few hours, preferably not more than two hours. In everyday terms, one seeks a suspension with something akin to the consistency and stability of cream. That kind of suspension may be achieved in any convenient manner, but is best prepared by means of a high shear homogenizer.

Not excluded is the possibility that the part of the particulate solid materials which is to be slurried with granulating fluid can be any part thereof, thus some or all of any of the individual ingredients, or even just some of the entire unsegregated mixture. Empirically, the best results seem to be obtained when the material which is slurried is at least mostly active matter. This ties in with the tentative supposition that homogenization somehow improves the compression characteristics of the material being slurried because, as previously explained, the tabletting aids have already been selected for their beneficial effect upon the compression characteristics of the granulate and need little improvement in this respect, but the compression characteristics of the active matter often leave much to be desired.

As a rule of thumb it seems to be the case that the part of the particulate solid material which is homogenized with the chosen amount of granulating fluid should contain not more than 50% w/w, and usually not more than about 35% w/w, of the total active matter; but, on the other hand, it was found that the slurry should contain not less than 10% w/w and usually not less than about 15% w/w, of the total active matter.

Taking a different approach, it also seems to be the case that the part of the particulate solid material which is homogenized with the chosen amount of granulating fluid usually not exceed 50% w/w of the total particulate solid materials, and need not be more than about 35% w/w; but, on the other hand, usually will not be less than 10% w/w, and often not less than 15% w/w, of the total particulate solid material.

At this point it is appropriate to observe that the slurry granulation method of this invention naturally can be employed in the tabletting of any kind of active matter, even easily compressible kinds of active matter. This slurry granulation method however has been developed by us with the particular objective of improving the tabletting of poorly compressible active matter, and it is there that it displays itself to best advantage. Regrettably, there is no universally accepted definition or test which can be used to identify poorly compressible material, but any experienced tabletter will intuitively recognize what is meant thereby.

It is also appropriate here to observe that there is nothing which forbids the use of the slurry granulation method of this invention in the preparation of tablets containing only relatively low proportions of active matter; but, again, the improved method has been developed with the particular objective of facilitating the preparation of tablets containing higher-than-usual proportions of active matter, and it is in that area that the method shows itself in the most advantageous light. By "higher-than-usual" proportions of active matter we choose, somewhat arbitrarily, to mean tabletting mixtures and tablets made therefrom wherein the proportion of active matter relative to the whole (dry) mixture is 80% w/w or more.

While not always achievable, it has been found that using the present slurry granulation method makes it generally possible to form satisfactory tablets even from materials which are poorly compressible and/or present in higher-than-usual proportions while utilizing the levels of tabletting aids which would conventionally be employed in wet-granulation yet which would fail to be sufficient with such materials were it not for the slurry granulation technique of this invention.

Usable in the improved process of the invention are from 5% to 25% w/w, and often only from 5% to 15% w/w, of tabletting aids overall; and within those overall ranges some or all of the following:
binders in the range of from 2% to 10% w/w;
glidants in the range of from 0.2% to 10% w/w;
lubricants in the range of from 0.2% to 4% w/w and
disintegrants in the range of from 2% to 10% w/w.

Obviously, the process of the invention displays its advantages most outstandingly when the active matter is poorly compressible and needs (at least for some clinical purposes) to be present in higher-than-usual proportions. Examples of medicinally active matters which fall in this dual-problem category are for instance:

(a) nalidixic acid, that is, 1-ethyl-1,4-dihydro-7-methyl-4-oxo-1,8-naphthyridine-3-carboxylic acid; and (b) paracetamol, that is, N-(4-hydroxyphenyl)acetamide, with or without methionine, that is 2-amino-4-(methylthio)butyric acid; and (c) hexopal, that is, myo-inositol hexa-3-pyridine-carboxylate; and (d) benorylate, that is, 2-(acetyloxy)benzoic acid 4-(acetylamino)phenyl ester; and (e) paracetamol methionate, that is, N-acetyl-para-aminophenyl N'-acetyl-methionate.

Besides the immediately obvious candidates for the slurry granulation process of this invention which have been mentioned above there are of course others which suggest themselves such as the sulphonamides.

The chosen amount of granulating fluid used to form the slurry will be in the range of from 90% up to 100% by weight of the previously predetermined total quantity already discussed above. If there is any uncertainty about quite how much granulating fluid will be needed, then a little can be held back (thus not included in the slurry) to be added at discretion after the slurry has been incorporated into the mix. Except in that situation it is however preferred that the "chosen amount" should be substantially the same as the "predetermined quantity"; because, for reasons presently not fully understood, it does seem that in order to secure the maximum improvement in the compression characteristics of the final granulate it is desirable that the chosen amount of granulating fluid used in formation of the slurry should be substantially all of the predetermined quantity, so that thus the resultant slurry will alone be substantially sufficient to achieve the desired moist, coherent but non-pasty mass containing all the ingredients, without the need for any significant further addition of granulating fluid. Thus, it is preferred to use all or virtually all of the granulating fluid to form the slurry.

The lower end of the weight percentage of solids in the slurry, set at a minimum of about 25% w/w, is perhaps somewhat arbitrary; but some such lower limit is needed to ensure that the proportion of the total particulate solid materials which undergoes the slurrying step is sufficient to achieve the objectives of this invention. The upper end of the weight percentage of solids has no theoretical maximum, but is limited purely by the increasing practical difficulties of forming the slurry and using it to moisten the particulate solids mix as the percentage w/w of solids rises. In plain language, what one does is to form a slurry with as high a percentage w/w of solids as can conventionally be achieved and utilized. Though perhaps not impossible it seems rather unlikely that the percentage w/w of solids in the slurry will ever exceed 80% w/w, and preferably ever significantly exceed about 70%. Preferably used is a slurry having a percentage w/w of solids in the range of from 40% up to 60% w/w; and, particularily preferred is a percentage w/w of solids of around 50% w/w, thus say 50±5% by weight.

The granulating fluid used in the improved method of this invention to form the slurry and thereafter to moisten the mixture must, as previously indicated, be substantially non-solvent for the overwhelming proportion (at least 90% w/w, and usually 95% w/w or more) of the particulate solid material(s) to be moistened thereby. That requirement however does not necessarily mean that the granulating fluid used in the method must be inherently non-solvent for all the ingredients. On the contrary, it is indeed a possible and sometimes preferred feature of the method of this invention that the non-solvent granulating fluid should be or should include a liquid which inherently is a solvent for some of the ingredients, provided only that the inherently solvent fluid is rendered substantially non-solvent by substantially saturating or even super-saturating it with that solute.

Nevertheless, it is in fact often quite desirable that the otherwise non-solvent granulating fluid should serve as a solvent for a minor proportion of the tabletting aids. Specifically, we have found it usually advantageous if at least part of the binding agent, and normally all of it, is dissolved in the granulating fluid incorporated in the granulating slurry.

Examples of such conventional binding agents include the following, namely starch, soluble starch, gelatin, polyvinylpyrrolidone or a cellulose derivative. Of all the various binding agents we have so far employed the best by far, possibly because of its wide-ranging solubility profile in fluids, has proved to be polyvinylpyrrolidone (PVP), which therefore we much prefer to employ and desirably dissolved in the continuous phase of the granulating slurry.

It will of course be appreciated that, as in conventional practice, the granulating fluid employed to form the granulating slurry can sometimes advantageously consist of or include a substantially non-toxic, organic liquid more volatile than water, and in that event the process should be carried out if appropriate under flame-proof conditions. In those cases where an ingredient or ingredients partly dissolve in the granulating fluid, it may be desirable or even sometimes preferred to include a crystal inhibitor in the mixture being processed. Thus, for example, lactose or more preferably sodium acetate may be included as a crystal inhibitor.

Dependent upon the nature of the various particulate solid ingredients and other operating parameters, the granulating fluid employed can be any of those used in conventional wet granulation techniques, and thus, for instance, it can comprise or include one or more of water, methanol, ethanol, isopropyl alcohol, acetone and/or methyl ethyl ketone; and, further, it can comprise or include any of one or more water-immisicible, relatively volatile organic liquids, for example, methylene chloride, chloroform or ether.

When seeking to achieve one of the primary objectives of this invention, namely the preparation of tablets containing higher-than-usual proportions of active matter, there will be no call for incorporation of mere bulking agents, which are preferably omitted. There is however no other objection to the incorporation of bulking agents in the particulate solid materials used in the process of this invention. Supposing that any such bulking agents are to be included those selected may of course be any of the conventional ones, chosen in accordance with prevailing practice, and thus will probably consist of or include one or more of the following, namely lactose, calcium phosphate, mannitol starch and/or soluble starch.

After the remaining part of the particulate solid materials has been uniformly moistened by means of the granulating slurry, the resultant moist, coherent, non-pasty mass is broken down into moist granules in any conventional manner, usually by screening.

The moist granules must then be dried. Drying can be effected by any convenient method, and various conventional drying techniques available, for example, drying either in loosely packed drying trays, or more conveniently in a fluidised-bed dryer.

The process of this invention will normally include the step of blending the tabletting granules with one or more further tabletting aids before compacting the granulate to form tablets in conventional tabletting machinery. These post-granulation tabletting aids will usually consist of or include one or more disintegrants or lubricants. Such disintegrants may consist of or include a component or mixture of components capable of imparting an effervescent character to the final tablet, but in that event all the parameters of the process must of course be chosen so as to form the final tablet without detriment to its desired effervescent character.

This invention of course also extends to tabletting granulates and also tablets made therefrom whenever prepared in or by the process herein disclosed.

In addition, the invention also provides a tablet of overall weight no more than about 1 g, which tablet comprises a unit dose of active matter of at least about 700 mg, the active matter being paracetamol together with methionine or paracetamol methionate, or paracetamol methionate alone, present in an amount of from 80 to 90% be weight, and the tablet having a hardness of from 7 to 15 kp, a friability of less than 2%, preferably less than 1%, and affording a disintegration time of no more than 15 minutes, preferably from 5 to 15 minutes.

In order that the invention may be more fully understood it will now be described in more detail, though only by way of illustration, with reference to the following examples:

EXAMPLE 1

Preparation of Tablets Containing Paracetamol and DL-Methionine using Wholly Aqueous Granulating Slurry

Stage A: Preparation of Tabletting Mixture

A tabletting mixture was formed by mixing together the ingredients which are listed in Table I below, in the absolute and proportionate amounts also shown in Table I, by means of the procedure described subsequently herein:

TABLE I

| Ingredients | Total Quantity in grams | Amount in Slurry |
|---|---|---|
| ACTIVE MATTER | | |
| DL-Methionine | 250 | 125 |
| Paracetamol | 500 | — |
| (Sub-Total of Active Matter) | (750) | (125) |
| TABLETTING AIDS | | |
| Polyvinylpyrrolidone | 30 | 30 |
| Stearic acid | 10 | — |
| Sodium Starch Glycollate | 50 | — |
| (Sub-Total of Tabletting Aids) | (90) | (30) |
| TOTAL: | 840 | 155 |
| Granulating Fluid: | Water: 200 mls | 200 grams |

Stage B: Preparation of the Granulate

The procedure used for the preparation of the granulate from the above-listed ingredients was as follows:

Preparation of the Slurry:

The polyvinylpyrrolidone (30 grams) was dissolved in 200 mls of water. Half of the DL-methionine (i.e. 125 grams) was suspended therein by means of a high-shear homogenizer to form a stable dispersion having a cream-like consistency, which is used as the granulating slurry in the manner described below.

Preparation of the Moist Mass:

The remainder of the DL-methionine (i.e. 125 grams) was mixed with the paracetamol (500 grams) and half the sodium starch glycollate (25 grams) in a conventional mixer-granulator. The mixture was then wet granulated until suitably massed in an otherwise conventional manner except that as granulating fluid there was used the granulating slurry prepared as described in Stage A above.

Preparation of the Granules:

The resultant moist, coherent, non-pasty granulate was screened through a 4-mesh sieve, and dried in a fluidized bed drier at a temperature of about 50°–60° C. until a moisture-content of less than 2% had been achieved.

The resulting dried granules were re-screened through a 16-mesh sieve to eliminate agglomerates and then blended with stearic acid (10 grams) and the remainder of the sodium starch glycollate (25 grams) to form the final granulate ready for tabletting.

Stage C: Preparation of Tablets

The free-flowing tabletting granulate prepared as described in Stage B above was fed into a suitable conventional tablet-press, and compacted thereby into tablets which had an overall weight of approximately 850 mg each. Despite the fact that paracetamol is poorly compressible and DL-methionine still more so, yet these were together present to an extent of nearly 90% w/w, with only about 10.7% of tabletting aids and no mere bulking agents, these tablets were found to conform to accepted standards of hardness, fragility, disintegration and uniformity of weight.

EXAMPLE 2

Preparation of Tablets containing Paracetamol and Methionine, using Non-Aqueous or Semi-Aqueous Granulating Fluids

Stage A: Choice of Ingredients of Mixture

A tabletting mixture was formed, by the procedure described below, from the ingredients listed together with their absolute and proportionate amounts in Table II as follows:

TABLE II

| Ingredients | Quantity in Mixture (grams) | Amount in Slurry (grams) |
|---|---|---|
| ACTIVE MATTER: | | |
| DL-Methionine | 250 | 125 |
| Paracetamol | 500 | — |
| (Sub-Total of Active Matter) | (750) | (125) |
| TABLETTING AIDS: | | |
| Sodium Starch Glycollate | 50 | |
| Stearic Acid | 10 | |
| Polyvinylpyrrolidone | 30 | 30 |
| (Sub-Total of Tabletting Aids) | (90) | (30) |
| TOTALS: | 840 | 155 |
| Granulating Fluid | Water and various Isopropanol/Water mixtures 200 mls | 200 grams (water) |

Stage B¹: Preparation of Comparative Granulate by Conventional 'Wet Granulation'

A preliminary run, using the above-listed ingredients in a standard mixer-granulator, established that approximately 200 mls of water (containing the polyvinylpyrrolidone) added as granulating fluid in the conventional manner were needed to obtain the desired moist, coherent, non-pasty mass suitable for granulation.

The mass was then granulated by screening and drying in a fully conventional manner.

Stage B²: Preparation of Granulate by 'Slurry Granulation' in Accordance with the Present Invention Using a standard mixer-granulator, the above-listed ingredients were brought together in the following manner:

Preparation of the Slurry:

The polyvinylpyrrolidone (30 grams) was dissolved in the predetermined amount, namely 200 mls, of one of the following granulating fluid systems:
(a) isopropanol:
(b) a mixture (80:20 v/v) of isopropanol and water:
(c) a mixture (60:40 v/v) of isopropanol and water:
(d) a mixture (40:60 v/v) of isopropanol and water: and
(e) a mixture (20:80 v/v) of isopropanol and water.

Dissolution was carried out at room temperature under flame-proof conditions, since the flashpoint of isopropanol is only 55° F. (about 13° C.).

Under the same conditions, half of the DL-methionine (i.e. 125 grams) was suspended therein by means of a high-shear homogenizer to form a stable dispersion having a cream-like consistency, which was used in the manner described below as a granulating slurry in the formation of tablets.

Preparation of the Moist Mass:

The remainder of the DL-methionine (125 grams) was mixed with the paracetamol (500 grams) and half of the sodium starch glycollate (25 grams) in a conventional mixer-granulator. The dry mixture was then wet granulated until suitably massed in an otherwise conventional manner except that as the granulating fluid for that purpose there was used the granulating slurry prepared as described above.

Preparation of the Granules:

The resultant moist, coherent, non-pasty granulate was screened through a 4-mesh sieve, and dried in an fluidized-bed air-drier at a temperature of about 40° C. for a period of about 20 minutes until the odor of isopropanol had disappeared.

The resultant dried granules were re-screened through a 16-mesh sieve to eliminate agglomerates and then blended with the stearic acid (10 grams) and the rest of the sodium starch glycollate (25 grams) so as to form the final granulate.

Stage C¹: Preparation of Comparative Tablets

The granulate prepared as described in Stage B¹ above was compressed into 840 mg tablets upon a suitable conventional rotary tabletting machine. The resultant tablets were however unsatisfactory, due to major problems of the flow of the granulate to the dies and of lamination or splitting of the compressed tablets.

Stage C²: Preparation of Tablets according to This Invention

The granulate prepared as described in Stage B² above was fed to the same conventional rotary tabletting machine, and there compressed to form 840 mg tablets. These were found to conform to accepted standards of hardness, fragility, disintegration and uniformity of weight.

EXAMPLE 3

Preparation of Tablets containing both Paracetamol and Paracetamol Methionate using Methanol as the Granulating Fluid Stage A: Preparation of Tabletting Mixture A tabletting mixture was formed by mixing together the ingredients which are listed in Table III below, in the absolute and proportionate amounts also shown in Table III, by means of the procedure described subsequently herein.

TABLE III

| Ingredients | Ingredients Quantity in Whole Mixture (grams) | Amount in Slurry (grams) |
|---|---|---|
| ACTIVE MATTER: | | |
| Paracetamol Methionate | 428 | 55 grams |
| Paracetamol | 400 | 50 grams |
| (Sub-Total of Active Matter) | (828) | (105 grams) |
| TABLETTING AIDS: | | |
| Sodium Starch Glycollate | 100 | — |
| Magnesium Stearate | 8 | — |
| Polyvinylpyrrolidone | 50 | 50 grams |
| Sodium Lauryl Sulphate | 2 | — |
| (Sub-Total of Tabletting Aids) | (160) | (50 grams) |
| TOTALS: | 988 | 155 grams |
| Granulating Fluid: | Methanol: 300 mls | 237.7 grams |

Stage B¹: Preparation of Comparative Granulate by Conventional Moist Granulation A preliminary run, using the above-listed ingredients (excepting 50 grams of the sodium starch glycollate and 8 grams of magnesium stearate and 2 grams of sodium lauryl sulphate) in a standard mixer-granulator established that approximately 300 mls of methanol (containing the polyvinylpyrrolidone) added as granulating fluid in the conventional manner were needed to obtain the desired moist, coherent, non-pasty mass suitable for granulation.

The mass was then granulated by screening and drying in a fully conventional manner.

Stage B²: Preparation of Granulate in Accordance with this Invention

Using a standard mixer-granulator, the above-listed ingredients were brought together in the following manner:

Preparation of the Slurry

The polyvinylpyrrolidone (50 grams) was dissolved in the full amount of methanol predetermined in Stage B¹ above, namely 300 mls.

Dissolution was carried out at room temperature under flame-proof conditions, since the flashpoint of methanol is only 54° F. (about 13° C.).

Under the same conditions, a proportion of both the paracetamol methionate (i.e. 55 grams) and the paracetamol (i.e. 50 grams) was suspended in the PVP-containing methanol by means of a high-shear homogenizer, to form a stable dispersion having a cream-like consistency, which was used in the manner described below as a granulating slurry in the formation of tablets.

Preparation of the Moist Mass

The remainder of the paracetamol methionate (i.e. 373 grams) was mixed with the remainder of the paracetamol (350 grams) and half of the sodium starch glycollate (50 grams) in a conventional mixer-granulator, and this dry mixture was wet-granulated (under flame-proof conditions) until suitably massed in a conventional manner except that as the granulating fluid there was used the granulating slurry prepared as described above.

Preparation of the Granules

The resultant moist, coherent, non-pasty mass was screened through a 4-mesh sieve, and dried in a fluidized-bed air-drier at a temperature of about 40° C. until the odor of methanol had disappeared.

The resultant dried granules were re-screened through a 16-mesh sieve to eliminate agglomerates; and they were then blended with the remainder of the sodium starch glycollate (50 grams), with the sodium lauryl sulphate (2 grams) and with the magnesium stearate (8 grams) so as to form the final granulate ready for tabletting.

Stage C[1]: Preparation of Comparative Tablets

The granulate prepared as described in Stage B[1] above was compressed into 988 mg tablets upon a conventional rotary tabletting machine. The resultant tablets were however unsatisfactory, due to flow and lubrication problems with the granulate and lamination of the tablets.

Stage C[2]: Preparation of Tablets according to this Invention

The free-flowing tabletting granulate prepared as described in Stage B[2] above was fed into the same rotary tabletting machine; and was compacted thereby into tablets which had an overall weight of 988 mg each, and which were found (despite the fact that they contained only approximately 16% of tabletting aids) to conform to the accepted standards of hardness, fragility, disintegration and uniformity of weight.

TABLE A

| Type of composition | Appearance | Hardness (kg) | Disintegration time (minutes) | Friability |
|---|---|---|---|---|
| Example 1 | Satisfactory | 11 to 13 | 11 to 13 | Satisfactory i.e. less than 1% |
| Example 1 | " | 8 | 5 | Satisfactory i.e. less than 1% |
| Example 1 | " | 15 | 12.5 | Satisfactory i.e. less than 1% |
| Example 3 | " | 14 to 15 | 4 to 10 | Satisfactory i.e. less than 1% |

EXAMPLE 4

Preparation of Tablets containing Benorylate using either Ethanol or Water as the Granulating Fluid in the Granulating Slurry Stage A: Preparation of Tabletting Mixture A tabletting mixture was formed by mixing together the ingredients which are listed in Table IV below, in the absolute and proportionate amounts also shown in Table IV, by means of the procedure described subsequently herein:

TABLE IV

| Ingredients | Quantity in Whole Mixture (grams) | Amount in Slurry (grams) |
|---|---|---|
| ACTIVE MATTER: | | |
| Benorylate | 750 | 250 |
| (Sub-Total of Active Matter | (750) | (250) |
| TABLETTING AIDS: | | |
| Polyvinylpyrrolidone | 18.75 | 18.75 |
| Potassium Sorbate | 0.75 | 0.75 |
| Maize Starch | 23 | — |
| Sodium Starch Glycollate | 21.75 | — |
| Magnesium Stearate | 3.75 | — |
| (Sub-Total of Tabletting Aids) | (68) | (19.5) |
| TOTAL: | 818 | 269.5 |
| Granulating Fluid: | Ethanol: 350 mls | 285.6 grams |

Stage B: Preparation of the Granulate

The procedure used for the preparation of the granulate from the above-listed ingredients was as follows:

Preparation of the Slurry

The polyvinylpyrrolidone (18.75 grams) and the potassium sorbate (0.75 grams) were dissolved in ethanol (350 ml). One third of the benorylate (250 grams) was then suspended in the ethanolic solution by means of a high-shear homogenizer, for form a stable dispersion having a cream-like consistency, which is used as the granulating slurry in the manner described below.

Preparation of the Moist Mass

The remainder of the benorylate (500 grams) was mixed with the maize starch (23 grams) in a conventional mixer-granulator. The mixture was then wet-granulated until suitably massed in an otherwise conventional manner except that as granulating fluid there was used the granulating slurry prepared as described above.

Preparation of the Granulate

The resultant moist, coherent, non-pasty granules were screened through a 4-mesh sieve, and dried in a fluidized-bed air-drier at a temperature of 40°–50° C. until the odor of ethanol had disappeared.

The resultant dried granules were re-screened through a 16-mesh sieve to eliminate agglomerates; and they were then blended with sodium starch glycollate (21.75 grams) and magnesium stearate (3.75 grams) so as to form the final granulate.

Stage C: Preparation of Tablets according to this Invention

The free-flowing tabletting granulate, prepared as described in Stage B above, was fed into a conventional rotary tabletting machine, and compressed to form 818 mg caplets. These were found to conform to accepted standards of hardness, fragility, disintegration and uniformity of weight.

The same procedure utilizing water (350 ml=350 grams) as the granulating fluid instead of ethanol, and drying the granules to a moisture content of less than 2%, yielded equally satisfactory caplets.

EXAMPLE 5

Preparation of Tablets containing Nalidixic Acid, using Isopropanol of Ethanol or Aqueous (50:50) Mixtures thereof as the Granulating Fluid in the Granulating Slurry

Stage A: Preparation of Tabletting Mixture

A tabletting mixture was formed by mixing together the ingredients which are listed in Table V below, in the absolute and proportionate amounts shown in Table V, by means of the procedure described subsequently herein:

TABLE V

| Ingredients | Quantity in Whole Mixture (grams) | Amounts in Slurry (grams) |
|---|---|---|
| ACTIVE MATTER: | | |
| Nalidixic Acid | 500 | 165 |
| (Sub-Total of Active Matter) | (500) | (165) |
| TABLETTING AIDS: | | |
| Polyvinylpyrrolidone | 37 | 37 |
| Maize Starch | 138 | — |
| Dicalcium Phosphate | 100 | — |
| Magnesium Stearate | 2 | — |
| (Sub-Total of Tabletting Aids) | (277) | (37) |
| TOTALS: | 777 | 202 |
| Granulating Fluid: | Isopropanol: 200 mls | 157 grams |

Stage B: Preparation of the Granulate

The procedure used for the preparation of the granulate from the above-listed ingredients was as follows:

Preparation of the Slurry

The polyvinylpyrrolidone (37 grams) was dissolved in the isopropanol (200 mls = 157 grams). About one-third of the nalidixic acid (165 grams) was then suspended in the isopropanol solution by means of a high-shear homogenizer, to form a stable dispersion having a cream-like consistency, which was used as the granulating slurry in the manner described below.

Preparation of the Moist Mass

The remainder of the nalidixic acid (335 grams) was mixed with the maize starch (138 grams) and the dicalcium phosphate (100 grams) in a conventional mixer-granulator. The mixture was then wet granulated until suitably massed in an otherwise conventional manner except that as the granulating fluid there was used the granulating slurry prepared as described above.

Preparation of the Granulate

The resultant moist, coherent, non-pasty granules were screened through a 4-mesh sieve, and dried in a fluidized-bed air-drier at a temperature of about 50°-60° C. until the of isopropanol could no longer be detected.

The resultant dried granules were re-screened through a 16-mesh sieve to eliminate agglomerates; and they were then blended with the magnesium stearate (2 grams) so as to form the final granulate.

Stage C: Preparation of Tablets according to this Invention

The free-flowing tabletting granulate, prepared as described in Stage B above was fed into a conventional rotary tabletting machine, and compressed to form both 777 mg tablets and 777 mg caplets. These were found to conform to accepted standards of hardness, fragility, disintegration and uniformity of weight.

The same procedure yielded equally satisfactory tablets and caplets when as the granulating fluid instead of isopropanol there was employed the same volume of ethanol (156 grams) or of aqueous (50:50) isopropanol (178.5 grams) or of aqueous (50:50) ethanol (178 grams).

EXAMPLE 6

Preparation of Tablets containing Hexopal using Ethanol as the Granulating Fluid in the Granulating Slurry A tabletting mixture was formed by mixing together the ingredients which are listed in Table VI below, in the absolute and proportionate amounts also shown in Table VI, by means of the procedure described subsequently herein.

TABLE VI

| Ingredients | Quantity in Whole Mixture (grams) | Amounts in Slurry (grams) |
|---|---|---|
| ACTIVE MATTER: | | |
| meso-Inositol Hexanicotinate | 1000 | 300 |
| (Sub-Total of Active Matter) | (1000) | (300) |
| TABLETTING AIDS: | | |
| Polyvinylpyrrolidone | 50 | 50 |
| Maize Starch | 75 | — |
| Sodium Lauryl Sulphate | 10 | — |
| Magnesium Stearate | 8 | — |
| (Sub-Total of Tabletting Aids) | (143) | (50) |
| TOTALS: | 1143 | 350 |
| Granulating Fluid: | Ethanol: 300 mls | 240 grams |

Stage B: Preparation of the Granulate

The procedure for the preparation of the granulate from the above-listed ingredients was as follows:

Preparation of the Slurry

The polyvinylpyrrolidone (50 grams) was dissolved in the ethanol (300 ml = 240 grams). Roughly a third of the meso-inosital hexanicotinate (300 grams) was then suspended in the ethanolic solution by means of a high-shear homogenizer, to form a stable dispersion having a cream-like consistency, which is used as the granulating slurry in the manner described below.

Preparation of the Moist Mass

The remainder of the meso-inositol hexanicotinate (700 grams) was then placed in a conventional mixer-granulator and wet-granulated until suitably massed in an otherwise conventional manner except that as the granulating fluid there was used the slurry prepared as described above.

Preparation of the Granulate

The resultant moist, coherent, non-pasty granules were screened through a 4-mesh sieve, and dried in a fluidized-bed air-drier at a temperature of about 50°-60° C. until the odor of ethanol could no longer be detected.

The resultant dried granules were re-screened through a 16-mesh sieve to eliminate agglomerates; and they were then blended with the maize starch (75 grams), the sodium lauryl sulphate (10 grams) and the magnesium stearate (8 grams) so as to form the final granulate.

Stage C: Preparation of Tablets according to this Invention

The free-flowing tabletting granulate, prepared as described in Stage B above, was fed into a conventional rotary tabletting machine, and compressed to form 1143 mg caplets. These were found to conform to accepted standards of hardness, fragility, disintegration and uniformity of weight.

EXAMPLE 7

Alternative Preparation of Tablets containing both Paracetamol and Paracetamol Methionate using Methanol as the Granulating Fluid

Stage A: Preparation of Tabletting Mixture

A tabletting mixture was formed by mixing together the ingredients which are listed in Table VII below, in the absolute and proportionate amounts also shown in Table VII, by means of the procedure described subsequently herein.

TABLE VII

| Ingredients | Quantity in Whole Mixture (grams) | Amount in Slurry (grams) |
|---|---|---|
| ACTIVE MATTER: | | |
| Paracetamol Methionate | 428 | 55 grams |
| Paracetamol | 400 | 50 grams |
| (Sub-Total of Active Matter) | (828) | (105 grams) |
| TABLETTING AIDS: | | |
| Sodium Starch Glycollate | 100 | — |
| Magnesium Stearate | 8 | — |
| Polyvinylpyrrolidone | 50 | — |
| Sodium Lauryl Sulphate | 2 | — |
| Sub-Total of Tabletting Aids) | (160) | (NIL) |
| TOTALS: | 988 | 105 grams |
| Granulating Fluid: | Methanol: 300 mls | 237.7 grams |

Stage B[1]: Preparation of Comparative Granulate by Conventional Moist Granulation A preliminary run, using the above-listed ingredients (excepting 50 grams of the sodium starch glycollate and 8 grams of magnesium stearate and 2 grams of sodium lauryl sulphate) in a standard mixer-granulated established that approximately 300 mls of methanol added as granulating fluid in the conventional manner were needed to obtain the desired moist, coherent, non-pasty mass suitable for granulation.

The mass was then granulated by screening and drying in a fully conventional manner.

Stage B[2]: Preparation of Granulate in accordance with this Invention

Using a standard mixer-granulator, the above-listed ingredients were brought together in the following manner:

Preparation of the Slurry

Working under flame-proof conditions at room temperature, since the flashpoint of methanol is only 54° F. (about 13° C.), a proportion of both the paracetamol methionate (i.e. 55 grams) and the paracetamol (i.e. 50 grams) was suspended in the full amount of methanol predetermined in Stage B[1] above, namely 300 mls, by means of a high-shear homogenizer, to form a stable dispersion having a cream-like consistency, which was used in the manner described below as a granulating slurry in the formation of granulates.

Preparation of the Moist Mass

The remainder of the paracetamol methionate (i.e. 373 grams) was mixed with the remainder of the paracetamol (350 grams) half of the sodium starch glycollate (50 grams) and all the polyvinylpyrrolidone (50 grams) in a conventional mixer-granulator, and this dry mixture was wet granulated (under flame-proof conditions) until suitably massed in a conventional manner except that as the granulating fluid there was used the granulating slurry prepared as described above.

Preparation of the Granules

The resultant moist, coherent, non-pasty mass was screened through a 4-mesh sieve, and dried in a fluidized-bed air-drier at a temperature of about 40° C. until the odor of methanol had disappeared.

The resultant dried granules were re-screened through a 16-mesh sieve to eliminate agglomerates; and they were then blended with the remainder of the sodium starch glycollate (50 grams), with the sodium lauryl sulphate (2 grams) and with the magnesium stearate (8 grams) so as to form the final granulate ready for tabletting.

Stage C[1]: Preparation of Comparative Tablets

The granulate prepared as described in Stage B[1] above was compressed into 988 mg tablets upon a conventional rotary tabletting machine. The resultant tablets were however unsatisfactory, due to flow and lubrication problems with the granulate and lamination of the tablets.

Stage C[2]: Preparation of Tablets according to this Invention

The free-flowing tabletting granulate prepared as described in Stage B[2] above was fed into the same rotary tabletting machine; and was compacted thereby into tablets which had an overall weight of 988 mg each, and which were found (despite the fact that they contained only approximately 16% of tabletting aids) to conform to the accepted standards of hardness, fragility, disintegration and uniformity of weight.

EXAMPLE 8

Preparation of Tablets containing Paracetamol using Water as the Granulating Fluid in the Granulating Slurry A tabletting mixture was formed by mixing together the ingredients which are listed in Table VIII below, in the absolute and proportionate amounts also shown in Table VIII, by means of the procedure described subsequently herein.

TABLE VIII

| Ingredients | Quantity in Whole Mixture (grams) | Amounts in Slurry (grams) |
|---|---|---|
| ACTIVE MATTER: | | |
| Paracetamol | 500 | 150 |
| (Sub-Total of Active Matter) | (500) | (150) |
| TABLETTING AIDS: | | |
| Polyvinylpyrrolidone | 3 | 3 |
| Sorbitol Powder | 100 | 75 |

TABLE VIII-continued

| Ingredients | Quantity in Whole Mixture (grams) | Amounts in Slurry (grams) |
|---|---|---|
| Carbowax 6000 | 12 | 12 |
| Stearic Acid | 4 | — |
| Talc | 20 | — |
| Maize Starch | 17 | — |
| Soluble Starch | 35 | — |
| (Sub-Total of Tabletting Aids) | (191) | (90) |
| TOTALS: | 691 | 240 |
| Granulating Fluid: | Water: 100 mls | 100 grams |

[Note: Carbowax 6000 is believed to be a mixture of polyethylene glycols and methoxypolyethylene glycols having an average molecular weight of approximately 6,000].

Stage B: Preparation of the Granulate

The procedure used for the preparation of the granulate from the above-listed ingredients was as follows:

Preparation of the Slurry

The polyvinylpyrrolidone (3 grams) and three-quarters of the sorbitol powder (75 grams) were dissolved in water (100 ml=100 grams). Roughly a third of the paracetamol (150 grams) and the Carbowax 6000 (12 grams) were then suspended in the aqueous solution by means of a high-shear homogenizer, to form a stable dispersion having a cream-like consistency, which is used as the granulating slurry in the manner described below.

Preparation of the Moist Mass

The remainder of the paracetamol (350 grams) was mixed with the soluble starch (35 grams) and the rest of the sorbitol powder (25 grams) in a conventional mixer-granulator. The mixture was then wet-granulated until suitably massed in an otherwise conventional manner except that as the granulating fluid there was used the granulating slurry prepared as described above.

Preparation of the Granulate

The resultant moist, coherent, non-pasty granules were screened through a 4-mesh sieve, and dried in a fluidized-bed air-drier at a temperature of 50°-60° C. until the moisture level had dropped below 2% w/w.

The resultant dried granules were re-screened through a 16-mesh sieve to eliminate agglomerates; and they were then blended with the talc (20 grams), stearic acid (4 grams) and maize starch (17 grams) so as to form the final granulate.

Stage C: Preparation of Tablets according to this Invention

The free-flowing tabletting granulate, prepared as described in Stage B above, was fed into a conventional rotary tabletting machine, and compressed to form one-half inch diameter tablets. These were found to conform to accepted standards of hardness, fragility, disintegration and uniformity of weight.

EXAMPLE 9

Preparation of Caplets Containing Paracetamol and DL-Methionine using Wholly-Aqueous Granulating Slurry

Stage A: Preparation of Tabletting Mixture

A tabletting mixture was formed by mixing together the ingredients which are listed in Table IX below, in the absolute and proportionate amounts also shown in Table IX, by means of the procedure described subsequently herein:

TABLE IX

| Ingredients | Total Quantity in grams | Amount in Slurry |
|---|---|---|
| ACTIVE-MATTER | | |
| DL-Methionine | 250 | 125 |
| Paracetamol | 500 | — |
| (Sub-Total of Active Matter) | (750) | (125) |
| TABLETTING AIDS | | |
| Polyvinylpyrrolidone | 30 | 30 |
| Sodium acetate | 13 | 13 |
| Stearic acid | 10 | — |
| Sodium Starch Glycollate | 50 | — |
| (Sub-Total of Tabletting Aids) | (68) | (43) |
| TOTAL: | 853 | 168 |
| Granulating Fluid | Water: 85 mls | 85 grams |

Stage B: Preparation of the Granulate

The procedure used for the preparation of the granulate from the above-listed ingredients was as follows:

Preparation of the Slurry

The sodium acetate (13 grams) was dissolved in 85 mls of water and the polyvinylpyrrolidone (30 grams) was dissolved in the aqueous solution of sodium acetate. Half of the DL-methionine (i.e. 125 grams) was suspended in the thus-formed aqueous solution by means of a high-shear homogenizer to form a stable dispersion having a cream-like consistency, which was used as the granulating slurry in the manner described below.

Preparation of the Moist Mass:

The remainder of the DL-methionine (i.e. 125 grams) was mixed with the paracetamol (500 grams) and half the sodium starch glycollate (25 grams) in a conventional mixer-granulator. The mixture was then wet-granulated until suitably massed in an otherwise conventional manner except that as granulating fluid there was used the granulating slurry prepared as described in Stage A above. (If required a small amount of additional water may be added to achieve the moistmass condition).

Preparation of the Granules:

The resultant moist, coherent, non-pasty granulate was screened through a 4-mesh sieve, and dried in a fluidized-bed drier at a temperature of about 60° until a moisture-content of 1.5% to 2% w/w had been achieved.

The resulting dried granules were re-screened through a 16-mesh sieve to eliminate agglomerates and then blended with stearic acid (10 grams) and the remainder of the sodium starch glycollate (25 grams) to form the final granulate ready for tabletting.

Stage C: Preparation of Tablets

The free-flowing tabletting granulate prepared as described in Stage B above was fed into a suitable conventional tablet-press fitted with caplet tooling, and compacted thereby into caplets which had an overall weight of approximately 853 mg each. Despite the fact that paracetamol is poorly-compressible and DL-methionine still more so, yet these were together present to an extent of nearly 88% w/w, with only about 12% of tabletting aids and no mere bulking agents. Furthermore, these caplets were found to conform to accepted standards of appearance, hardness, fragility (friability), disintegration and uniformity of weight as can be seen for three different batches from the results given in Table B below:

temperature and under the same conditions, a proportion of both the paracetamol methionate (i.e. 42.8

TABLE B

| Batch | Uniformity of Weight | Appearance | Hardness (kp) | Disintegration time (minutes) | Fragility (Friability) |
|---|---|---|---|---|---|
| A | Satisfactory ±5% | Satisfactory | 14.7 | Satisfactory - less than 15 minutes* | Satisfactory - 0.05% weight loss |
| B | Satisfactory ±5% | " | 8.7 | Satisfactory - less than 15 minutes* | Satisfactory - 0.12% weight loss |
| C | Satisfactory ±5% | " | 12.7 | Satisfactory - less than 15 minutes* | Satisfactory - 0.12% weight loss |

*British Pharmacopoeia Standard BP 1980

EXAMPLE 10

Preparation of Tablets containing both Paracetamol and Paracetamol Methionate using water as the Granulating Fluid Stage A: Preparation of Tabletting Mixture A tabletting mixture was formed by mixing together the ingredients which are listed in Table X below, in the absolute and proportionate amounts also shown in Table X, by means of the procedure described subsequently herein.

TABLE X

| Ingredients | Quantity in Whole Mixture (grams) | Amount in Slurry (grams) |
|---|---|---|
| ACTIVE MATTER: | | |
| Paracetamol methionate | 428 | 42.8 |
| Paracetamol | 400 | 40 |
| (Sub-Total of Active Matter) | (828) | (82.8) |
| TABLETTING AIDS: | | |
| Sodium starch glycollate | 100 | — |
| Magnesium stearate | 8 | — |
| Polyvinylpyrrolidone | 40 | 40 |
| Sodium lauryl sulphate | 10 | 10 |
| (Sub-Total of Tabletting Aids) | (158) | (50) |
| TOTALS: | 986 | 132.8 |
| Granulating Fluid: | Water: 310 mls | 310 grams |

STAGE B[1]: Preparation of Comparative Granulate by Conventional Moist Granulation A preliminary run, using the above-listed ingredients (excepting 50 grams of the sodium starch glycollate and 8 grams of magnesium stearate) in a standard mixer-granulator established that approximately 310 mls of water (containing the polyvinylpyrrolidone and sodium lauryl sulphate) added as granulating fluid in the conventional manner were needed to obtain the desired moist, coherent, non-pasty mass suitable for granulation.

The mass was then granulated by screening and drying in a fully conventional manner.

Stage B[2]: Preparation of Granulate in accordance with this invention

Using a standard mixer-granulator, the above-listed ingredients were brought together in the following manner:

Preparation of the Slurry

The polyvinylpyrrolidone (40 grams) and sodium lauryl sulphate (10 grams) were dissolved in the full amount of water predetermined in Stage B[1] above, namely 310 mls. Dissolution was carried out at room temperature and under the same conditions, a proportion of both the paracetamol methionate (i.e. 42.8 grams) and the paracetamol (i.e. 40 grams) was suspended in the PVP- and sodium lauryl sulphate-containing water by means of a high-shear homogenizer, to form a stable dispersion having a cream-like consistency, which was used in the manner described below as a granulating slurry in the formation of granulate.

Preparation of the Moist Mass

The remainder of the paracetamol methionate (i.e. 385.1 grams) was mixed with the remainder of the paracetamol (360 grams) and half of the sodium starch glycollate (50 grams) in a conventional mixer-granulator, and this dry mixture was wet-granulated until suitably massed in a conventional manner except that as the granulating fluid there was used the granulating slurry prepared as described above.

Preparation of the Granules

The resultant moist, coherent, non-pasty mass was screened through a 4-mesh sieve, and dried in a fluidized-bed air-drier at a temperature of about 55° C. to a moisture content of about 1.5% w/w.

The resultant dried granules were re-screened through a 16-mesh sieve to eliminate agglomerates. They were then blended with the remainder of the sodium starch glycollate (50 grams) and with the magnesium stearate (8 grams) so as to form the final granulate ready for tabletting.

Stage C[1]: Preparation of Comparative Tablets

The granulate prepared as described in Stage B[1] above was compressed into approximately 986 mg tablets upon a conventional rotary tabletting machine. The resultant tablets were however unsatisfactory, due to flow and lubrication problems with the granulate, and to lamination of the tablets.

Stage C[2]: Preparation of Tablets according to this Invention

The free-flowing tabletting granulate prepared as described in Stage B[2] above was fed into the same rotary tabletting machine. The granulate was compacted thereby into tablets which had an overall weight of approximately 986 mg each, and which were found (despite the fact that they contained only approximately 16% of tabletting aids) to conform to accepted standards of appearance, hardness, fragility, (friability) disintegration and uniformity of weight.

I claim:

1. In a process for manufacturing granulate which may be formed into tablets by compressing and compacting a suitable granulate, wherein the granulate is prepared by forming an intimate mixture of particulate solid materials including poorly compressible medicinally active matter and tabletting aids, as well as other pharmacologically inert materials, thereafter wet granulating said mixture by moistening it with non-solvent granulating fluid to form a substantially uniform, moist, coherent, non-pasty mass which finally is granulated and dried, these dried granules, after optionally adding further tabletting aids thereto, constituting the desired granulate ready for compression and compaction into tablets, the improvement which comprises:

(A) predetermining the quantity of granulating fluid needed to convert the entire particulate solid mixture into a moist, coherent, non-pasty mass;

(B) homogenizing part only of the particulate solid material, separately from the remainder thereof, with a chosen amount of granulating fluid, that chosen amount being at least 90% by weight of the aforesaid predetermined quantity of granulating fluid, so as to form a substantially homogenous slurry wherein the percentage by weight of solids in the slurry is at least 25% w/w and (C) moistening the remaining part of the particulate solid material in the manner of wet granulation with the slurry resultant from step (B) above and thereafter with any remaining granulating fluid, so as thus to form a substantially uniform, moist, coherent, non-pasty mass ready for granulation.

2. A process according to claim 1, in which the active matter consists of one or more medicinally active substances.

3. A process according to claim 2, in which the homogenization into the form of a slurry is performed by means of a high-shear homogenizer.

4. A process according to claim 3, in which that part of the particulate solid material which is homogenized with the chosen amount of granulating fluid is or includes some or all of the active matter.

5. A process according to claim 4, in which the part of the particulate solid material which is homogenized with the chosen amount of granulating fluid comprises not more than 50% and not less than 10% by weight of the total active matter.

6. A process according to claim 5, in which that part of the particulate solid material which is homogenized with the chosen amount of granulating fluid comprises from 15% to 35% by weight of the total active matter.

7. A process according to claim 4, in which that part of the particulate solid material which is homogenized with the chosen amount of granulating fluid does not exceed 50% but is not less than 10% by weight of the total particulate solid material.

8. A process according to claim 7, in which that part of the particulate solid material which is homogenized with the chosen amount of granulating fluid is in the range of from 15% to 35% by weight of the total particulate solid material.

9. A process according to claim 8, in which that part of the particulate solid material which is homogenized with the chosen amount of granulating fluid comprises poorly compressible active matter.

10. A process according to claim 9, in which the particulate solid material contains 80% w/w or more of active matter.

11. A process according to claim 9, in which the total tabletting aids incorporated in the granulate before compression into tablets amount to from 5% to 25% w/w overall calculated relative to the weight of the final (dry) powder mass.

12. A process according to claim 11, in which the total tabletting aids amount to from 5% to 15% w/w overall.

13. A process according to claim 11, in which the tabletting aids present are some or all of the following:
binders in the range from 2% to 10% w/w;
glidants in the range of from 0.2% to 10% w/w;
lubricants in the range of from 0.2% to 4% w/w; and
disintegrants in the range of from 2% to 10% w/w.

14. A process according to claim 9, in which the active matter homogenized comprises at least one of the substances selected from the group consisting of nalidixic acid, paracetamol, a mixture of paracetamol and methionine, hexopal, benorylate and paracetamol methionate.

15. A process according to claim 14, in which the chosen amount of granulating fluid used in homogenization is substantially all of the predetermined quantity thereof, and thus the resultant slurry is alone sufficient to achieve the desired moist, coherent but non-pasty mass without the need for any significant further addition of granulating fluid.

16. A process according to claim 14, in which the percentage by weight of solids in the slurry does not exceed 80% w/w.

17. A process according to claim 16, in which the percentage by weight of solids in the slurry does not exceed 70% w/w.

18. A process according to claim 16, in which the percentage by weight of solids in the slurry is in the range of from 40% w/w up to 60% w/w.

19. A process according to claim 16, in which the percentage by weight of solids in the slurry is 50%±5% w/w.

20. A process according to claim 16, in which the tabletting aids employed include a binding agent at least part of which is dissolved in the granulating fluid incorporated in the slurry.

21. A process according to claim 16, in which the tabletting aids employed include polyvinylpyrrolidone serving as a binding agent.

22. A process according to claim 16, in which the granulating fluid employed to form the granulating slurry comprises one or more substantially non-toxic, organic liquids more volatile than water, and if appropriate the process is carried out under flame-proof conditions.

23. A process according to claim 16, in which the granulating fluid employed to form the granulating slurry comprises one or more selected from the group consisting of water, methanol, ethanol, isopropanol, acetone and methyl ethyl ketone.

24. A process according to claim 16, in which the granulating fluid employed to form the granulating slurry comprises one or more selected from the group consisting of methylene chloride, chloroform and ether.

25. A process according to claim 16, in which after the remaining part of the particulate solid material has been uniformly moistened by means of the granulating slurry, the resultant moist, coherent, non-pasty mass is broken down into moist granules by screening.

26. A process according to claim 25, in which the moist granules are dried in a fluidized-bed dryer.

27. A process according to claim 26, which includes the further step, after blending the dried granules with one or more further tabletting aids, of compacting the resultant granulate to form tablets of a predetermined tablet volume in conventional tabletting machinery.

* * * * *